United States Patent
Prattichizzo et al.

(10) Patent No.: US 11,285,291 B2
(45) Date of Patent: Mar. 29, 2022

(54) HAPTIC RING

(71) Applicant: WEART S.R.L., Milan (IT)

(72) Inventors: Domenico Prattichizzo, Siena (IT); Giovanni Spagnoletti, Molinara (IT); Guido Gioioso, Tricarico (IT)

(73) Assignee: WEART S.R.L., Milan (IT)

( * ) Notice: Subject to any disclaimer, the term of this patent is extended or adjusted under 35 U.S.C. 154(b) by 0 days.

(21) Appl. No.: 17/040,397

(22) PCT Filed: Mar. 22, 2019

(86) PCT No.: PCT/IB2019/052348
§ 371 (c)(1),
(2) Date: Sep. 22, 2020

(87) PCT Pub. No.: WO2019/180677
PCT Pub. Date: Sep. 26, 2019

(65) Prior Publication Data
US 2021/0060286 A1    Mar. 4, 2021

(30) Foreign Application Priority Data
Mar. 23, 2018  (IT) .......................... 102018000003965

(51) Int. Cl.
*H04B 3/36* (2006.01)
*A61M 21/00* (2006.01)
*G08B 6/00* (2006.01)

(52) U.S. Cl.
CPC .............. *A61M 21/00* (2013.01); *G08B 6/00* (2013.01); *A61M 2021/0022* (2013.01); *A61M 2209/088* (2013.01)

(58) Field of Classification Search
CPC .......... A61M 21/00; A61M 2021/0022; A61M 2209/088; G08B 6/00
(Continued)

(56) References Cited

U.S. PATENT DOCUMENTS 9,597,217 B2 *   3/2017   Patton ................. A63B 21/155
10,678,334 B1 *  6/2020   Pezent .................... G06F 3/013
(Continued)

FOREIGN PATENT DOCUMENTS

JP         2018010582 A    1/2018
WO    WO-2017029406 A1    2/2017
(Continued)

OTHER PUBLICATIONS

International Search Report and Written Opinion dated Jul. 19, 2019 in PCT/IB2019/052348, European Patent Office, Netherlands, 12 pages.
(Continued)

*Primary Examiner* — Zhen Y Wu
(74) *Attorney, Agent, or Firm* — Sterne, Kessler, Goldstein & Fox P.L.L.C.

(57) ABSTRACT

Device (100) for applying haptic stimuli to a body part (200) of a user, comprising a stiff support (30) configured to contact the body part 200; a containing element configured to keep the body part (200) in contact with the stiff support (30); an actuating element configured to push the stiff support (30) into the containing element and apply a pressure to the body part 200. The containing element comprises a stiff frame (10) defining a recess (20) to house the body part 200. The frame (10) comprises two lateral stiff guides (51) defining the recess (20) and the stiff support (30) is configured to move in a guided manner in the stiff guides (51). At least one servomotor (40, 40') is provided connected integrally to the stiff frame (10) on the opposite side to the stiff support (30) with respect to the recess (20) and arranged to cause a relative movement, inside the recess (20) and with respect to the lateral stiff rails (51), of the stiff support (30) with respect to the body part (200). At least one belt (50, 50') sliding parallel to the lateral stiff rails (51) and connected
(Continued)

respectively with the servomotor (40) and the stiff support (30) is provided. The servomotor (40) is configured to operate the or each belt (50, 50') to cause guided movement in the stiff guides (51) of the stiff support (30).

11 Claims, 7 Drawing Sheets

(58) Field of Classification Search
USPC .................................................... 340/407.1
See application file for complete search history.

(56) References Cited

U.S. PATENT DOCUMENTS

| | | | | |
|---|---|---|---|---|
| 10,713,907 | B2* | 7/2020 | Anderson | G06F 3/011 |
| 2006/0047342 | A1* | 3/2006 | Khoshnevis | G06F 3/014 |
| | | | | 623/17.16 |
| 2009/0096746 | A1* | 4/2009 | Kruse | G06F 3/017 |
| | | | | 345/156 |
| 2016/0034742 | A1* | 2/2016 | Kim | H04B 1/385 |
| | | | | 382/124 |
| 2017/0165567 | A1* | 6/2017 | Walters | G06F 3/016 |
| 2017/0168565 | A1* | 6/2017 | Cohen | A61B 5/0022 |
| 2017/0308165 | A1* | 10/2017 | Erivantcev | G06F 3/0346 |
| 2018/0280227 | A1* | 10/2018 | Quest | A61H 23/0263 |
| 2018/0296834 | A1* | 10/2018 | John | A61B 5/4836 |
| 2018/0318545 | A1* | 11/2018 | Jones | A61M 21/02 |
| 2019/0104953 | A1* | 4/2019 | Narasimhan | A61B 5/02225 |
| 2020/0035071 | A1* | 1/2020 | Anderson | F15B 15/10 |

FOREIGN PATENT DOCUMENTS

| | | |
|---|---|---|
| WO | WO-2017137930 A1 | 8/2017 |
| WO | WO-2017175868 A1 | 10/2017 |
| WO | WO-2019180677 A1 | 9/2019 |

OTHER PUBLICATIONS

Meli, L., et al., "The hBracelet: A Wearable Haptic Device for the Distributed Mechanotactile Stimulation of the Upper Limb," IEEE Robotics and Automation Letters 3(3):2198-2205, Institute of Electrical and Electronics Engineers, United States (Jul. 2018).

Hussain, I., et al., "A wearable haptic ring for the control of extra robotic fingers," Haptic Interaction; 323-325, Springer Nature Singapore, Netherlands (Jul. 2017).

* cited by examiner

FIG.1

| Ref. No. | Text Description |
|---|---|
| 10 | stiff frame |
| 20 | recess |
| 30 | normal direction with respect to body part |
| 33 | ends of the stiff support |
| 35 | guide |
| 40 | servomotors |
| 41 | gears |
| 41' | teeth of the gears |
| 42 | gears |
| 42' | teeth of the gears |
| 50 | belts |
| 51 | guides of the belts |
| 52 | first end of the belt |
| 53 | second end of the belt |
| 100 | device for application of haptic stimuli |
| 200 | body part |

FIG.1A

| Ref. No. | Text Description |
|---|---|
| 10 | stiff frame |
| 20 | recess |
| 30 | normal direction with respect to body part |
| 33 | ends of the stiff support |
| 35 | guide |
| 40 | servomotors |
| 41 | gears |
| 41' | teeth of the gears |
| 42 | gears |
| 42' | teeth of the gears |
| 50 and 50' | belts |
| 51 | guides of the belts |
| 52 | first end of the belt |
| 53 | second end of the belt |
| 100 | device for application of haptic stimuli |
| 200 | body part |

FIG.2

| Ref. No. | Text Description |
|---|---|
| 10 | stiff frame |
| 20 | recess |
| 30 | normal direction with respect to body part |
| 33 | ends of the stiff support |
| 35 | guide |
| 40 | servomotors |
| 41 | gears |
| 41' | teeth of the gears |
| 42 | gears |
| 42' | teeth of the gears |
| 50 and 50' | belts |
| 51 | guides of the belts |
| 70 | vibrating element |
| 100 | device for application of haptic stimuli |
| 200 | body part |

FIG.3

| Ref. No. | Text Description |
|---|---|
| 10 | stiff frame |
| 20 | recess |
| 30 | normal direction with respect to body part |
| 31 | face of the stiff support |
| 33 | ends of the stiff support |
| 35 | guide |
| 40 | servomotors |
| 41 and 42 | gears |
| 41' and 42' | teeth of the gears |
| 50 and 50' | belts |
| 51 | guides of the belts |
| 60 | heating/cooling element |
| 61 | first face of the heating/cooling element |
| 62 | second face of the heating/cooling element |
| 100 | device for application of haptic stimuli |
| 200 | body part |

FIG.4

| Ref. No. | Text Description |
|---|---|
| 10 | stiff frame |
| 20 | recess |
| 30 | normal direction with respect to body part |
| 33 | ends of the stiff support |
| 35 | guide |
| 36 | direction of rotation |
| 40 | servomotors |
| 43 and 44 | pulleys |
| 50 and 50' | belts |
| 51 | guides of the belts |
| 52 | first end of the belt |
| 53 | second end of the belt |
| 90 | hinge |
| 95 | inner portion of the stiff support |
| 100 | device for application of haptic stimuli |
| 200 | body part |

FIG.5

| Ref. No. | Text Description |
|---|---|
| 10 | stiff frame |
| 20 | recess |
| 30 | normal direction with respect to body part |
| 33 | ends of the stiff support |
| 35 | guide |
| 37 | direction of rotation |
| 40 | servomotors |
| 43 and 44 | pulleys |
| 45 and 46 | pulleys |
| 50 and 50' | belts |
| 51 | guides of the belts |
| 98 | portion of the stiff support |
| 100 | device for application of haptic stimuli |
| 200 | body part |

| Ref. No. | Text Description |
|---|---|
| 10 | stiff frame |
| 20 | recess |
| 30 | normal direction with respect to body part |
| 40 | servomotors |
| 41 | gears |
| 42 | gears |
| 50 | belts |
| 60 | heating/cooling element |
| 70 | vibrating element |
| 100 | device for application of haptic stimuli |

HAPTIC RING

SCOPE OF THE INVENTION

The present invention relates to an annular-shaped sensory stimulation device adapted to be worn by a patient for use in various fields, such as for example the field of virtual reality, the field of rehabilitation, and others.

DESCRIPTION OF THE PRIOR ART

Numerous devices capable of providing haptic stimuli to users, i.e. capable of inducing haptic perceptions, are known today. In particular, devices capable of providing haptic stimuli such as to communicate in a unique or combined manner information on temperature, pressure and roughness of a surface are known.

These devices are generally used in various sectors. For example, it is possible to use them in virtual environments to encourage the perceptive immersion of a user in it. These can be used in the medical field, for example where a surgeon has to drive a robot by remote control to perform remote surgical operations. In this case, the surgeon is able to perceive the interaction forces between the surgical robot and the patient through a haptic interface, which can be worn on the hand. For example, the surgeon can perceive the shape of a surface as well as its roughness.

These devices can also be used in research for manipulation purposes, or they can be used during rehabilitation sessions having healing purposes, such as the care of traumas due to strokes.

Through these devices it is also possible to provide thermal stimuli to the skin of a user.

An example of a known device is described in WO2017029406A1. In particular, this device is used to treat patients following a stroke, but it can be used also in the field of entertainment or of sports during training programs. The device can be worn on one or more fingers of one hand, and includes a Peltier cell element for the administration of thermal stimuli, a vibrating element to provide mechanical stimuli at high frequency values, a pneumatic element configured to vary its volume and thus applying pressure stimuli to the user.

However, such a device, although compact and small in size, requires a hydraulic circuit to supply the pneumatic element. The presence of the pneumatic circuit and the relative power supply entails a high degree of constructive complexity. Furthermore, such a complex device requires frequent maintenance aimed at avoiding the risk of breakage by allowing the fluid, inside the pneumatic circuit, to enter correctly and rapidly into the inflation chamber of the pneumatic element.

Moreover, for a correct operation of the thermal module and of the vibration module, the presence of an electrical circuit is required which, in addition to the pneumatic circuit, weighs down the overall device structure and entails problems of overall size and possibility of wearing it.

Moreover, since this device can be fixed by means of a strap to a body part of the user, it is subject to an unsafe assembly, thus reducing its reliability.

Another haptic ring device is described in "G. Spagnoletti, I. Hussain, C. Pacchierotti, G. Salvietti, D. Prattichizzo—The hRing: a haptic interface for an extra robotic finger. IEEE Haptic symposium, Philadelphia, USA, 2016." It provides a belt driven by two servomotors and positioned in direct contact with a user's finger. It is able to provide both normal and tangential forces to the finger.

The belt provides normal and tangential efforts to the finger by adhering directly to it. However, even here the ring is fixed by means of a strap to a part of the user's body, resulting in a poor stability. Moreover, flexibility of the strap makes the entire ring yielding, reducing the precision and speed of transmission of tactile stimuli. Finally, the device does not lend itself easily to applying further stimuli, such as for example thermal or vibrational stimuli.

SUMMARY OF THE INVENTION

It is an object of the present invention to provide a device for applying haptic stimuli to a body part of a user which allows to achieve greater flexibility and adaptability to the conditions of use with respect to the devices of the prior art.

These and other purposes are achieved by a device for applying haptic stimuli to a part of a user's body, the device comprising:
- a stiff support configured to come into contact with the body art,
- a containing element configured to keep the body part in contact with the stiff support,
- an actuating element configured to push the stiff support into the containing element and apply a pressure to the body part;

The characteristic of the invention being that:
- the containing element comprises a stiff frame defining a recess to house the body part,
- the frame includes two lateral stiff rails defining the recess and the stiff support is configured to move in a guided manner in the stiff guides,
- is expected at least a servomotor connected integrally with the stiff frame on the opposite side to the stiff support with respect to the recess and arranged to cause a relative movement, inside the recess and with respect to the lateral stiff guides, of the stiff support with respect to the body part,
- is expected at least a sliding belt parallel to the lateral stiff guides,
- said or each belt is connected respectively with the servomotor and with the stiff support,
- the servomotor is configured to operate the or each belt to cause guided movement in the stiff guides of the stiff support.

In this way, by means of the present invention, a device of simple construction is obtained which is well suited to parts of a user's body.

The fact that the stiff support is configured to come into contact with the part of the user's body by actuating a servomotor which actuates at least one belt, having respective ends connected to the servomotor and to the stiff support, makes the device particularly compact while providing at the same time an integral solution from an engineering point of view. This solution, unlike the prior art, does not require a containment strap in order to make the device wearable, to the advantage of a better precision in the transmission of tactile stimuli.

Unlike the prior art, since the conveyor belt slides within lateral guides, it prevents it from being in direct contact with the body part to be stimulated, delegating this function to the stiff support. Moreover, this avoids possible contaminations, due to the wear material, for example due to the greasing of the belt, which could occur in a direct contact between the belt and the body part.

In particular, by means of the present invention it is possible to provide the user with a wide range of perceptual stimuli through a device of reduced and light overall dimensions. In fact, differently from what is described in WO2017029406A1, the present invention solves the problem linked to the structural complexity favoring an engineering solution that can work without requiring connection cables to an external power supply, but can operate by means of a simple pocket battery, which can be integrated into the device, and designed to guarantee a duration necessary for performing the required applications.

Advantageously, the stiff support can move in a guided manner in stiff guides with a motion parallel to the guides.

This allows the application of normal forces to be transferred to the body part, through contact with the stiff support, as for example or in cases where it is desired to simulate a catching of an object.

According to another advantageous aspect of the invention, the stiff support is configured to move in a guided manner in the stiff guides with a motion orthogonal to the guides.

This characteristic allows to simulate tangential forces for example following the exploration of surfaces in which the perception of tangential contact forces is required.

According to a further advantageous aspect of the invention, the stiff support is configured to move in a guided manner in the stiff guides with a rotary motion with respect to the guides.

This allows exploration of virtual surfaces to be achieved by simulating angular variations of this surface.

In particular, the stiff support can advantageously move with a combined motion between a parallel, orthogonal and rotary motion with respect to the guides, thus obtaining simulations of complete spatiality of the perception of contact with surfaces.

According to an embodiment of the invention, a first and a second servomotor are provided configured to rotate in an independent and not concordant manner to give the stiff support a motion parallel to the guides, and in a concordant manner to give the stiff support an orthogonal motion to the guides or a rotary motion with respect to the guides.

The presence of distinct servomotors adapted to adjust the elongation of the belts provides flexibility of use of the device, thereby obtaining an enhanced use precision.

In particular, the stiff support can be a single-piece body with ends configured to slide in the guides.

This solution makes possible to obtain a constructively simple low cost solution.

Advantageously, the stiff support may be a body in two portions having an outer portion with ends configured to slide in the guides and an inner portion configured to rotate in the outer portion to perform the rotary motion relative to the guides.

In this way, a stiff support is obtained which has two degrees of freedom according to a compact constructive solution.

According to another advantageous solution, the stiff support can be a body in two portions having a first end portion configured to slide in one of the guides and a second end portion configured to slide in the other guide, the first and second portions engaging telescopically between them to perform the motion orthogonal to the guides.

According to further variants realization of the invention, the stiff support can be a combination of the aforementioned bodies.

According to a further embodiment of the invention, a vibrating element is in contact with the stiff support and is configured to transmit vibrotactile oscillations to the part of the shell through the stiff support.

In this way, the presence of a vibrating element, such as a voice coil, in contact with the stiff support, allows vibratory stimuli to be transferred to the body part in a wide range of frequencies. The possibility of providing vibration stimuli can be useful if the user is required to perceive a different "texture" of virtual surfaces.

In a further embodiment of the invention, a heating/cooling element can be provided integral with the stiff support and having a first face configured to contact the body part and a second face in contact with the support.

The presence of the heating/cooling element, allows to obtain a device for applying haptic stimuli that allows the perception of thermal sensations to parts of the body because, for example, of the interaction with thermally altered virtual environments. Moreover, the fact that the heating/cooling element is in contact, and therefore associated with it, also allows to move the heating/cooling element with the same degrees of movement with which the stiff support is configured.

According to a further advantageous embodiment of the invention, it may be provided a vibrating element in contact with the stiff support, the vibrating element being configured to transmit vibrotactile oscillations to the body part through the stiff support and a heating/cooling element fixed to the stiff support and having a first face configured to contact the body part and a second face in contact with the stiff support, the stiff support having a first face (31) in contact with the second face of the heating/cooling element and a second face in contact with the vibrating element.

This solution allows to obtain a device capable of providing sensations of force or displacement in combination with vibrotactile and/or thermal sensations, obtaining or a synergy of application in small spaces to the body part, with high precision with respect to the prior art.

Advantageously, the heating/cooling element can be a Peltier cell comprising a thermistor.

The presence of the thermistor can limit the inrush current and thus protect the cooling and/or heating circuit.

Advantageously, the vibrating element is selected from: a voice coil, a vibrating eccentric mass, a piezoelectric vibrator, a resonator.

Advantageously, a control unit is provided comprising a communication module capable of communicating with a remote control system, said control unit being configured to transmit operating signals to said servomotors, to said vibrating elements to said cooling/heating elements.

BRIEF DESCRIPTION OF THE DRAWINGS

Further characteristics and/or advantages of the present invention will become clearer with the following description of an embodiment thereof, given as a non-limiting example, with reference to the annexed drawings in which.

DESCRIPTION OF SOME PREFERRED EMBODIMENTS

Figure 1:
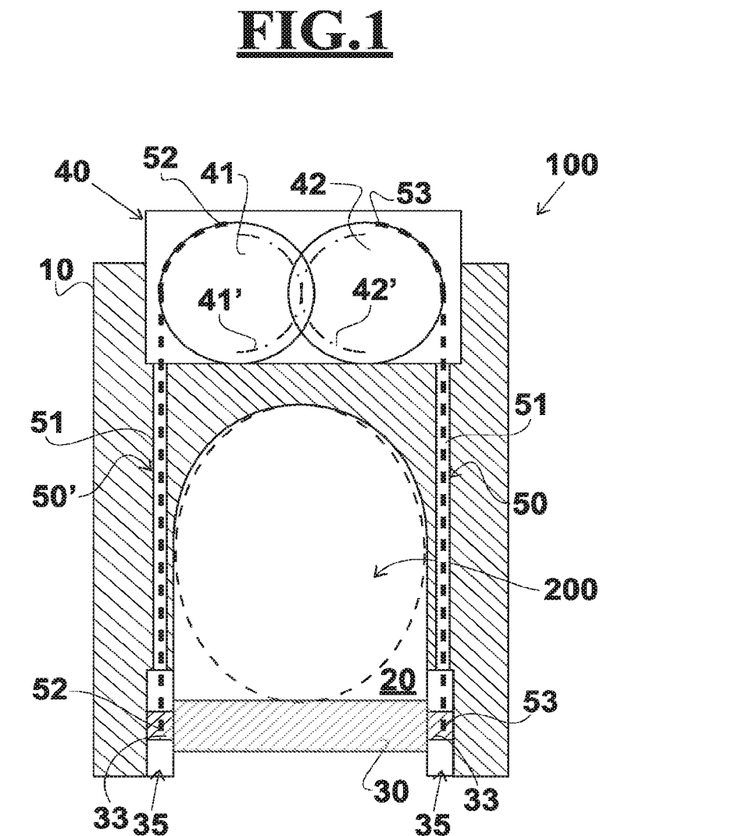
FIGS. 1, 1A show, according to a sectional view, a first embodiment of a device for applying haptic stimuli, comprising a stiff support in contact with a part of a user's body.

FIG. 1 describes an example of a device 100 for applying haptic stimuli to a body art 200 of a user.

The device 100 has a stiff frame 10 comprising a recess 20 adapted to house the part of a user's body 200. In particular, the part of the user's body 200 can be a fingertip, a phalanx, or a wrist, or an ankle, or another body part 200 capable of being enclosed in a ring and of receiving haptic stimuli of haptic type, in particular pressure, force, temperature.

Figure 1A:
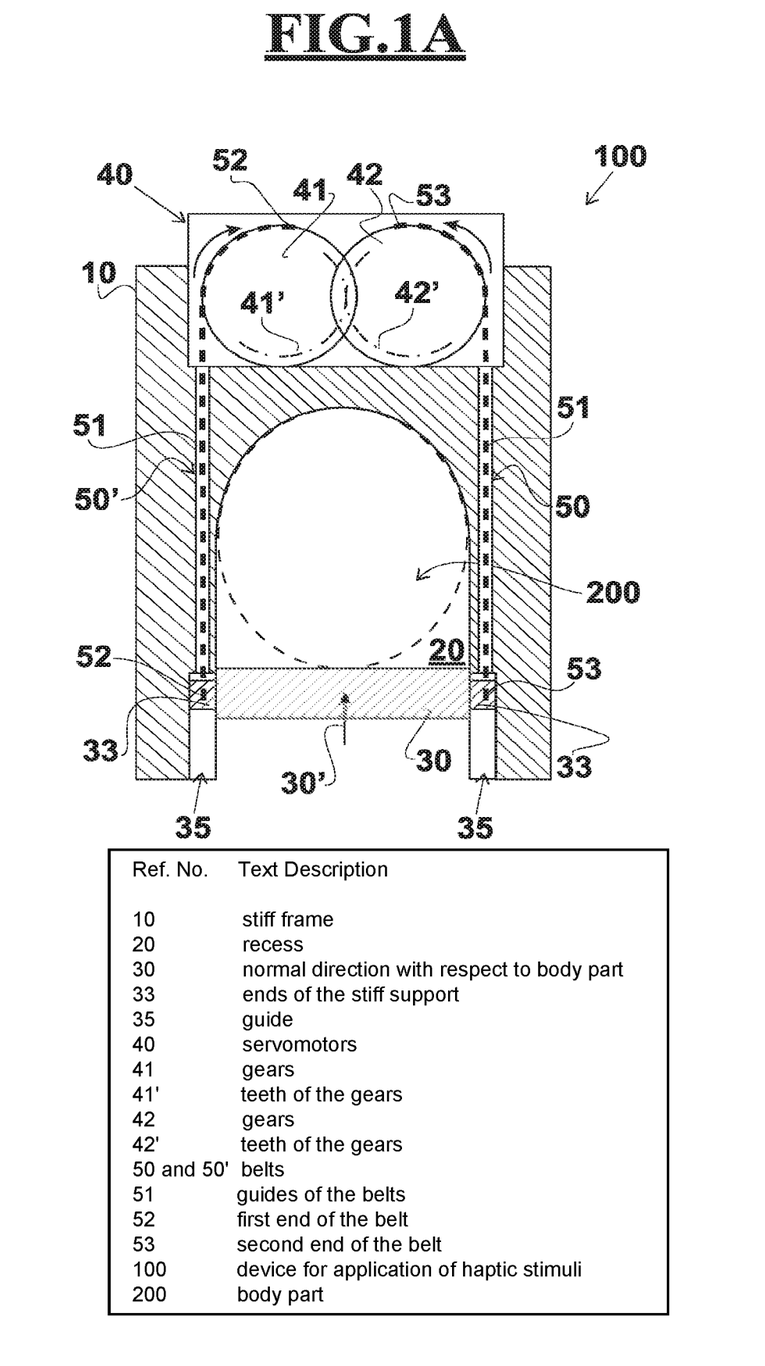

In the embodiment of FIGS. 1 and 1A the device 100 further comprises a stiff support 30 adapted to vary its relative position with respect to the body part 200 of the user. In particular, by means of a servomotor 40, for example arranged inside the stiff frame 10 or above it, it is possible to control the length of the belts 50 and 50'. In particular, the belts 50, 50' slide within respective channels 51 and are engaged, by means of a first end 52 to a circumferential portion of two respective gears 41, 42 or similar mechanisms, and by means of a second end 53 to the stiff support 30. A first gear 41, for example, can be rotated by the servomotor 40 and the second gear 42 is rotated by the first gear 41, for example by means of respective portions of teeth 41', 42'. Their not concordant rotation allows the belts 50, 50' to be wound or unwound simultaneously. In this way, through the meshing of the wheels 41, 42 according to a clockwise or anti-clockwise direction of rotation of the first gear 41 by means of the servomotor 40, an approaching motion or a distancing motion of the stiff support 30 with respect to the part of the user's body 200 is caused. The useful stroke of the stiff support 30 is limited to the meshing portion 41', 42' of the two wheels 41, 42 and is regulated by the presence of guides 35 within which the ends slide, for example prismatic ends 33, of the stiff support 30.

For example, the two wheels 41, 42 can mesh with each other with a transmission ratio 1:1 thus allowing the stiff support 30 to translate in a normal direction 30' with respect to the body part 200. This allows the stiff support to apply forces normal to the body part 200, required for example in virtual reality cases in which a simulation of the pressure on the body part 200 is desired, for example the fingertip to simulate the contact with a virtual body.

Figure 2:
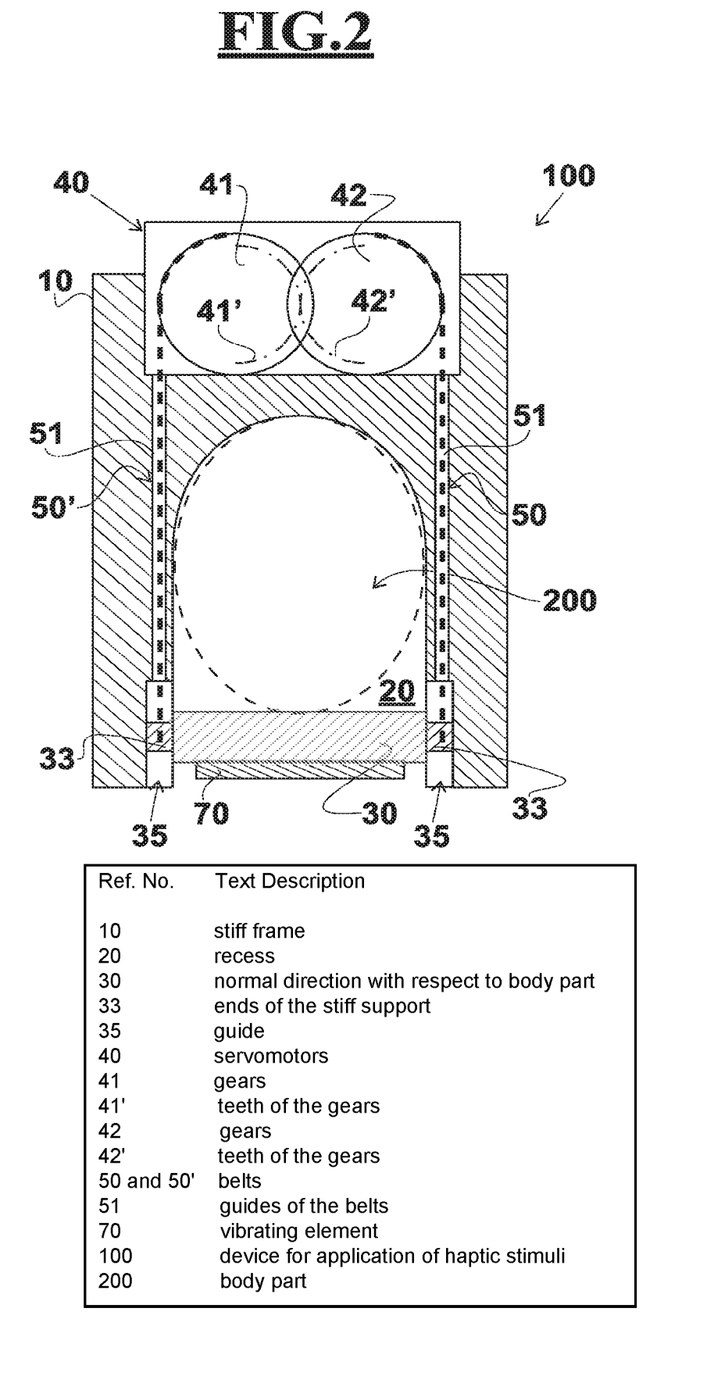
FIG. 2 shows, according to a sectional view, a second embodiment of a device for applying haptic stimuli, according to the invention, comprising a vibrating element in contact with a stiff support.

With reference to FIG. 2, a second embodiment of the invention is shown, similar to that of FIG. 1, in which a vibrating element 70 is associated with the stiff support 30.

In this way, the presence of a vibrating element 70, in contact with the stiff support 30, allows vibratory stimuli of various frequencies to be transferred to the body part 200. The possibility of providing vibration stimuli can be useful if the user is required to perceive a different "texture" of virtual surfaces.

For example, the vibrating element 70 can be a voice coil supplied with excitation current at frequency values similar to sound signals, or it can be an eccentric mass element or a piezoelectric actuator, or another type.

Figure 3:
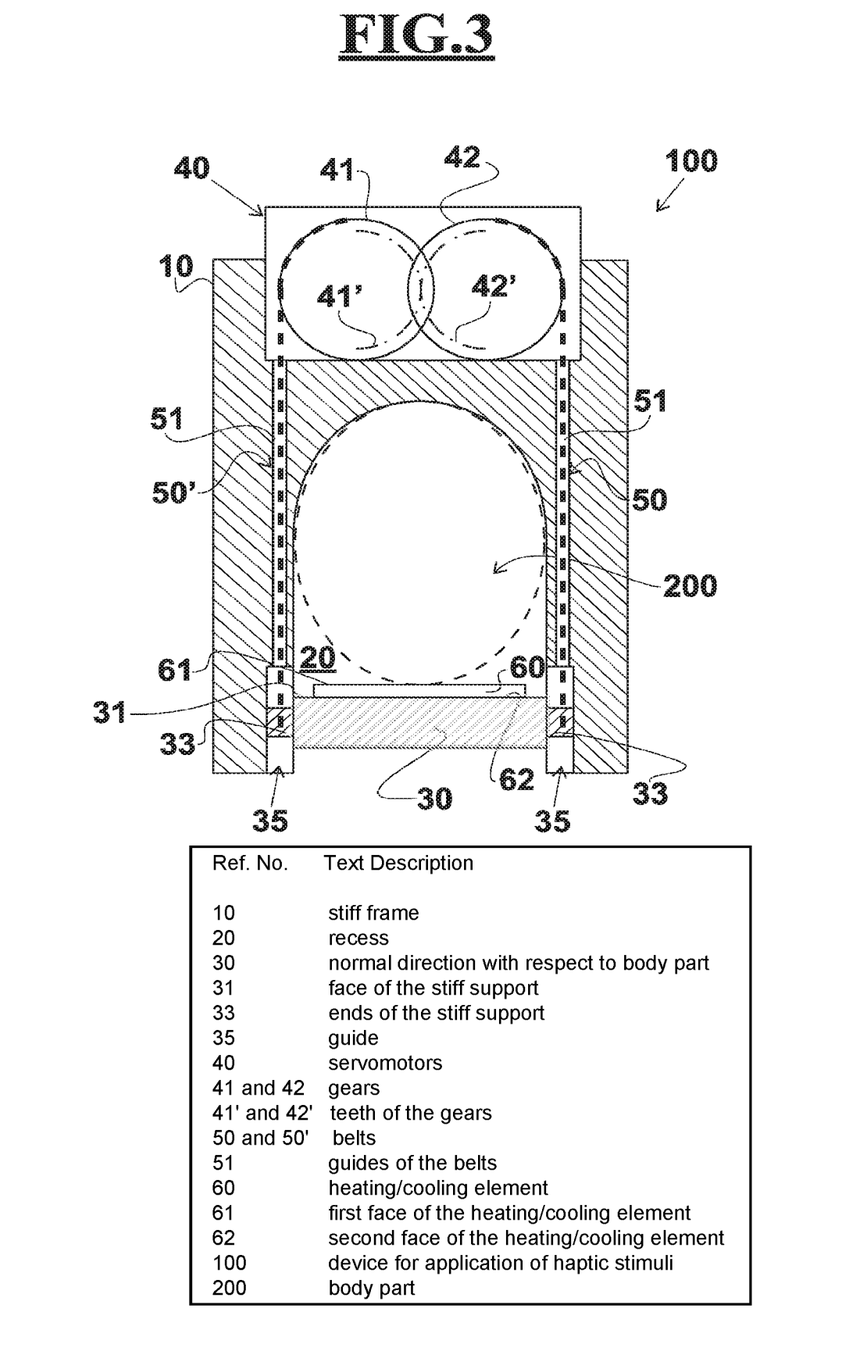
FIG. 3 shows, according to a sectional view, a third embodiment of a device according to the invention for the application of stimuli, comprising a heating/cooling element in contact with the stiff support.

With reference to FIG. 3, a third embodiment of the invention is shown, similar to that described in FIG. 2, in which the stiff support 30 is in contact, by means of a first face 31, with a second face 62 of a heating/cooling element, for example a Peltier cell 60.

The presence of a Peltier cell 60, or of another heating/cooling element, allows to have a thermal module which, in contact with the part of the user body 200 through a first face 61 thereof, can expand the range of stimuli that can be generated and can make thermal illusions possible.

It is also possible that the face 61 of the Peltier cell 60 comprises sectors whose temperature is controlled independently.

It is therefore possible, for example, to adjust the temperature of the Peltier cell 60 so as to perceive thermal variations in the body part 200 following the interaction with thermally altered virtual environments.

The Peltier cell 60 can comprise a thermistor, not shown in the figure, so as to limit the inrush current and thus protect the cooling and/or heating circuit.

In a manner not shown, an embodiment of the invention is possible which provides only the heating/cooling element and not the vibrating element.

In all three cases, there is the combination of the stiff support, which provides sensations of force or displacement in combination with vibrotactile and/or thermal sensations, obtaining a synergy of application in small spaces to the body part, with high precision with respect to the prior art.

Figure 4:
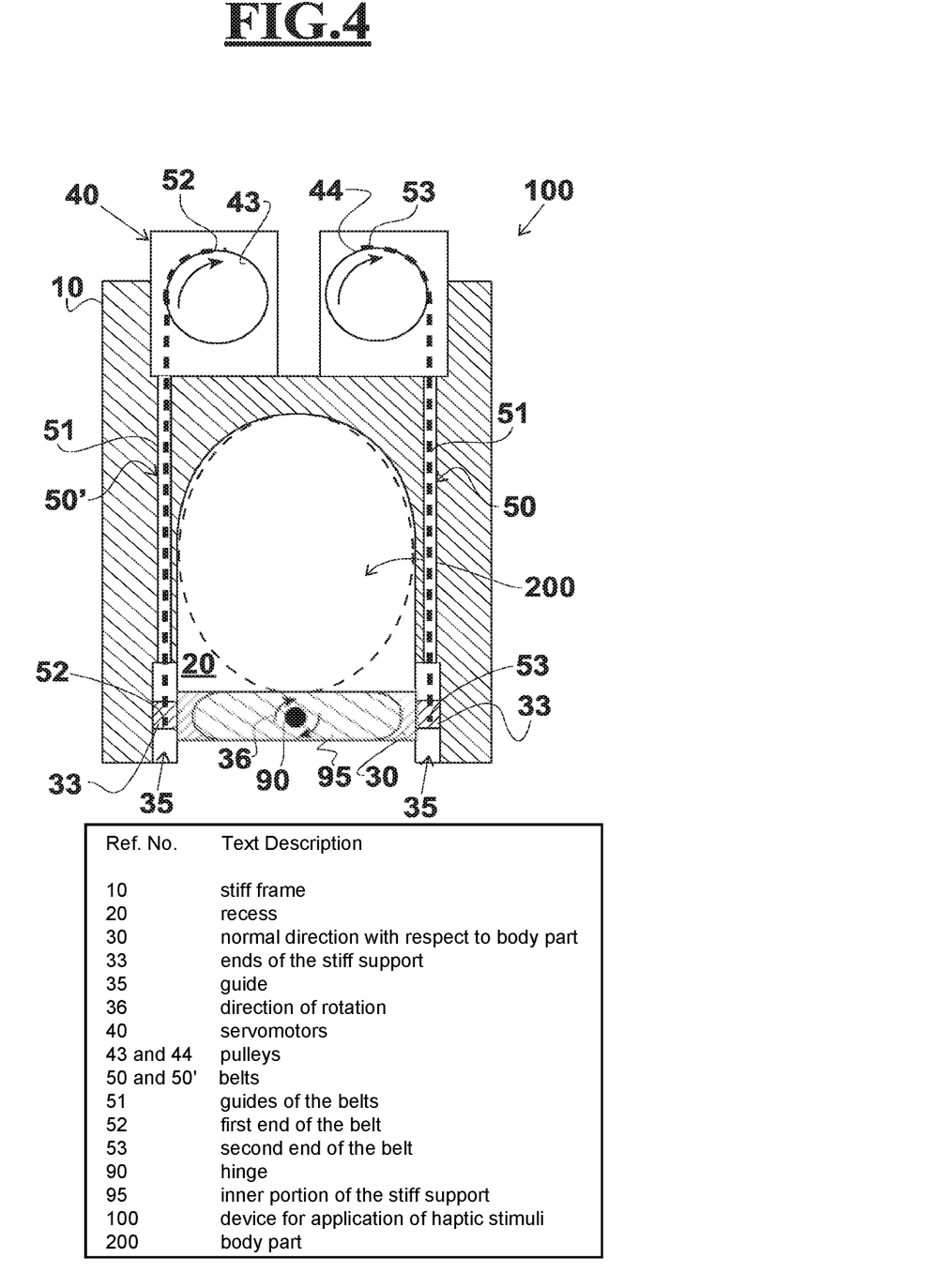
FIG. 4 shows, according to a sectional view, a possible alternative embodiment of a device for the application of haptic stimuli, according to the invention, in which the stiff support is a body divided in two portions.

With reference to FIG. 4, an alternative embodiment of the invention is described in which a first 40 and a second 40' servomotor are present, comprising respectively a first pulley at 43 and a second pulley 44. Similarly to what is described in FIG. 1, the belts 50, 50' are connected with pulleys 43, 44 through a first one ends 52 and by a second end 53 with the stiff support 30. The rotation of the pulleys 43, 44 can be independently regulated by the 40, 40' servomotors in synchronous concordant way, synchronous not concordant way or independent way. The stiff support 30 is for example constrained to a hinge 90 so that the rotation of the pulleys 43, 44 according to clockwise and/or anti-clockwise directions determines only an oscillation 36, only a translation or both. This allows a spatial exploration of a virtual surface by simulating angular variations of this surface.

In particular, the stiff support 30 is a body in two portions having an outer portion with ends 33 configured to slide in the stiff guides 51 and an inner portion 95 configured to rotate 36 in the outer portion to perform a rotary motion 36 with respect to the stiff guides 51.

Figure 5:
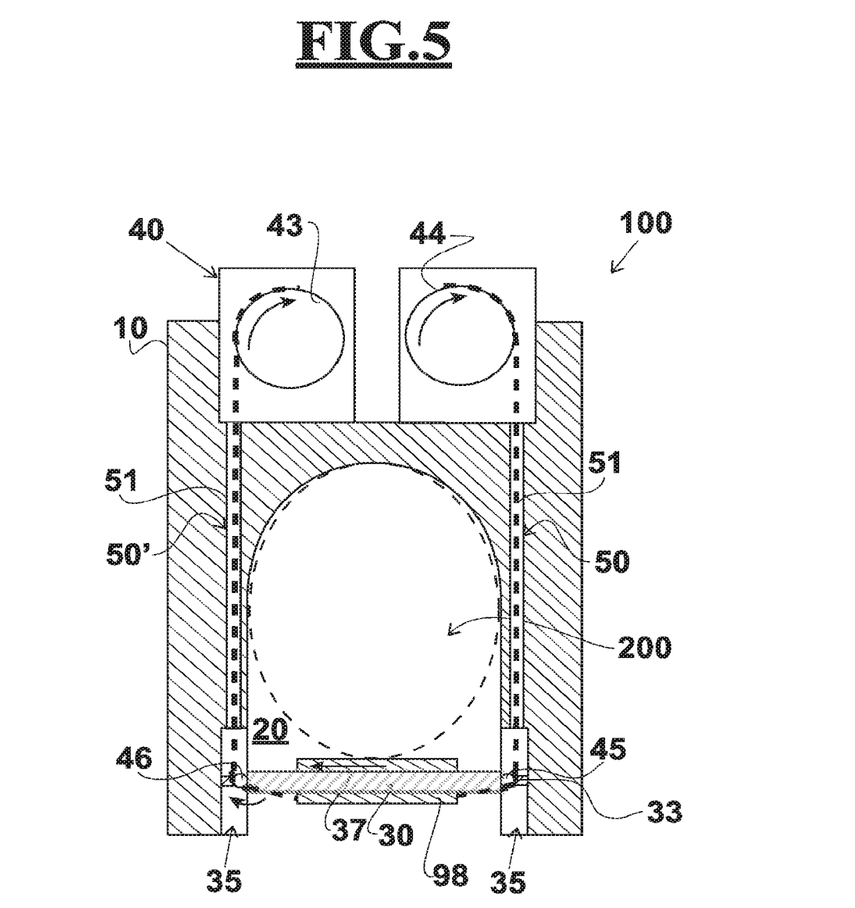
FIG. 5 shows, according to a sectional view, a further alternative embodiment of a device for the application of haptic stimuli, according to the invention, in which the stiff support is a body divided in two portions.

With reference to FIG. 5, an alternative embodiment of the invention is described in which the stiff support 30 is a body divided in two portions 30, 98 having a first portion 30 with an end 33 configured to slide in the stiff guides 51 and a second portion 98, external to the stiff support 30, configured to translate along the stiff support 30. In particular, the second portion carries out a movement of horizontal translation with respect to the stiff support 30 by means of transmitting pulleys 45, 46 within which respective belts 50, 50' slide, which on their turn engage with the second portion 98 so as to perform the orthogonal motion to the stiff guides 51.

Figure 6:
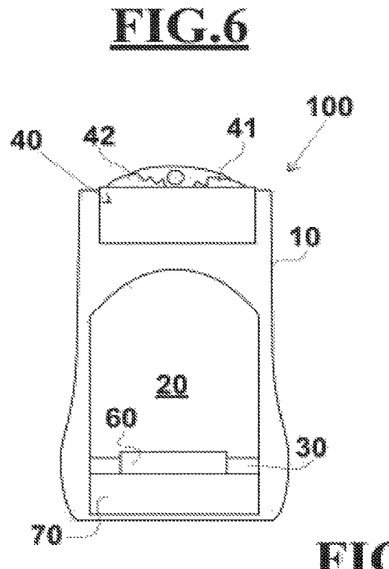
FIGS. 6, 6A, 6B show respective views, according to a preferred embodiment of the invention, of a device for the application of haptic stimuli.
Figure 6A:
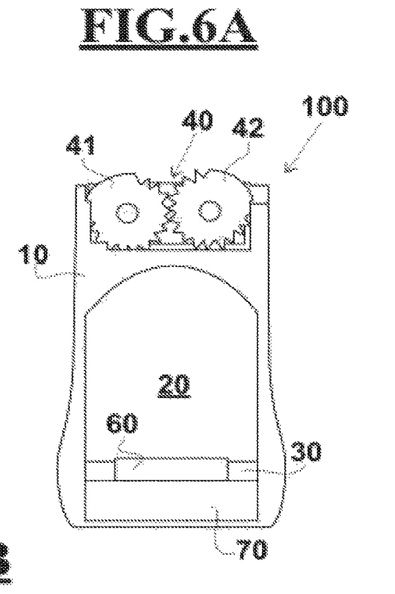
Figure 6B:
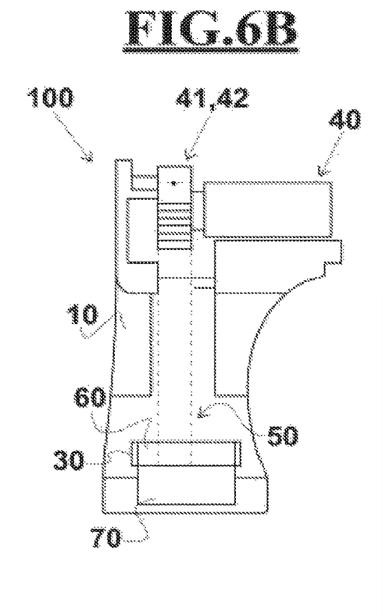

FIGS. 6, 6A, 6B show a preferred embodiment of the device 100, according to three views, comprising: the support drive, the heating/cooling element, the vibrating element.

In a manner not shown but easily implemented by a person skilled in the art, a control unit is provided comprising a communication action module capable of communicating with a remote control system, said control unit being configured to transmit operating signals to said servomotors, to said vibrating elements with said cooling/heating elements.

The above description of some specific embodiments is able to show the invention from a conceptual point of view so that others, using the known technique, will be able to modify and/or to adapt this specific embodiment in various applications without further researches and without departing from the inventive concept, and, therefore, it is understood that such adaptations and modifications will be considered equivalent to the specific embodiment. The means and materials for carrying out the described functions may be of various kinds without departing from the scope of the invention. It is understood that the expressions or terminology used are purely descriptive and therefore not limitative.

The invention claimed is:

1. A device for application of haptic stimuli to a body part of a user, said device comprising:
    a stiff support configured to contact said body part;
    a containing element configured to keep said body part in contact with said stiff support;
    an actuating element configured to push said stiff support in said containing element and to apply a pressure to said body part; wherein
    said containing element comprises a stiff frame defining a recess for housing said body part,
    said frame comprises two lateral stiff guides defining said recess, and said stiff support is configured to move in a guided way in said stiff guides;
    at least one servomotor is provided integrally connected to said frame opposite to said stiff support with respect to said recess and arranged to cause a relative movement, within said recess and with respect to said lateral stiff guides, wherein said stiff support with respect to said body part comprises,
    at least one belt arranged so that the at least one belt can slide parallel to said lateral stiff guides, wherein
    said at least one belt or each of said at least one belt is connected respectively with said servomotor and with said stiff support and
    said at least one servomotor is configured to operate said at least one belt or each of said at least one belt for causing said guided movement in said stiff guides of said stiff support.

2. The device according to claim 1, wherein said stiff support is configured to move in a guided way in said stiff guides with a movement selected from the group consisting of:
    a movement parallel to said guides;
    an orthogonal movement to said guides;
    a rotational movement with respect to said guides; and
    a combination thereof.

3. The device according to claim 1, wherein at least one servomotor comprises of a first and a second servomotor are provided configured to rotate independently in a non-concordant way for imparting to said stiff support a movement parallel to said guides, and in a concordant way for imparting to said stiff support a movement orthogonal to said guides or a rotational movement with respect to said guides.

4. The device according to claim 2, wherein said stiff support is selected from the group consisting of:
    a body arranged as an integral block having ends configured to slide in said guides,
    a body arranged as two portions having an external portion with ends configured to slide in said guides and an inner portion configured to rotate in said external portion for carrying out said rotational movement with respect to said guides,
    a body arranged as two portions having a first portion with an end configured to slide in one of said guides and a second portion with end configured to slide in the other one of said guides, the first and the second portion engaging slidingly on each other for carrying out said movement orthogonal to said guide; and
    a combination thereof.

5. The device according to claim 1, wherein a vibrating element is provided in contact with said stiff support and configured to transmit a vibrotactile oscillation to said body part through said stiff support.

6. The device according to claim 1, wherein a heating/cooling element is arranged integral to said stiff support and having a first face configured to contact with said body part and a second face in contact with said support.

7. The device according to claim 1, wherein a vibrating element is provided in contact with said stiff support and is configured to transmit vibrotactile oscillations to said body part through said stiff support, and a heating/cooling element is provided integral to said stiff support having a first face configured to contact with said body part and a second face in contact with said support, said stiff support having a first face in contact with said second side of said heating/cooling element and a second side in contact with said vibrating element.

8. The device according to claim 6, wherein said heating/cooling element is a Peltier cell.

9. The device according to claim 7 wherein said vibrating element is selected from a voice coil, a vibrating mass, a piezoelectric vibrator, or a resonator.

10. The device according to claim 1, wherein a control unit is provided comprising a communication module with a remote control system, said control unit is arranged to transmit operating signals to said at least one servomotor, to said vibrating elements and to said heating/cooling element according to commands transmitted from said remote control system.

11. The device according to claim 8, wherein the Peltier cell comprises a thermistor.

* * * * *